US00PP23108P3

(12) United States Plant Patent
Harris

(10) Patent No.: US PP23,108 P3
(45) Date of Patent: Oct. 16, 2012

(54) AZALEA PLANT NAMED 'MNIHAR014'

(50) Latin Name: ***Rhododendron* sp.**
Varietal Denomination: MNIHAR014

(75) Inventor: James O. Harris, Lawrenceville, GA (US); Ella Ruth Harris, legal representative, Lawrenceville, GA (US)

(73) Assignee: Ella Ruth Harris, Lawrenceville, GA (US), Executor of the Estate of James O. Harris ( * ) Notice: Subject to any disclaimer, the term of this patent is extended or adjusted under 35 U.S.C. 154(b) by 149 days.

(21) Appl. No.: 12/807,047

(22) Filed: Aug. 25, 2010

(65) Prior Publication Data

US 2012/0054929 P1 Mar. 1, 2012

(51) Int. Cl.
*A01H 5/00* (2006.01)

(52) U.S. Cl. ..... Plt./239

(58) Field of Classification Search ..... Plt./239, Plt./240

See application file for complete search history.

*Primary Examiner* — June Hwu

(74) *Attorney, Agent, or Firm* — Jondle & Associates, P.C.

(57) ABSTRACT

A new and distinct variety of Azalea plant with spring and fall blooming, attractive, showy, single mauve flowers, easily propagated by semi-hardwood cuttings in late spring through summer, moderate growth rate under normal fertilization and moisture conditions; broadly-rounded and freely-branching in habit, grows well in containers, thrives in shade or sun and is hardy in Zone 6, is disclosed.

2 Drawing Sheets

Genus and species: *Rhododendron* sp.
Variety denomination: 'MNIHAR014'.

BACKGROUND OF THE NEW PLANT

The present invention is a new and distinct variety of evergreen Azalea of the genus *Rhododendron*. This new Azalea, hereinafter referred to as 'MNIHAR014', was discovered in 2004 in Lawrenceville, Ga. 'MNIHAR014' originated from a planned cross hybridization in 1998 between the female azalea plant 'Martha Hitchcock' (unpatented) and the male azalea plant 'Conlec' (U.S. Plant Pat. No. 10,580) in a controlled environment in Lawrenceville, Ga. The present invention has a blooming period in spring and fall, broadly-rounded and compact growth habit, attractive and showy mauve colored flowers, and cold hardiness.

The new plant was first propagated by semi-hardwood cuttings in 2004 at a nursery in Dearing, Ga. and has been asexually propagated by semi-hardwood in Dearing, Ga. for over six years. The new plant retains its distinctive characteristics and reproduces true to type in successive asexual propagations by semi-hardwood cuttings.

Plant Breeder's Rights for this variety have not been applied for. 'MNIHAR014' has not been made publicly available or sold more than one year prior to the filing date of this application.

SUMMARY OF THE INVENTION

The following are the most outstanding and distinguishing characteristics of this new variety when grown under normal horticultural practices in Dearing, Ga.

1. Spring and fall blooming;
2. Attractive, showy, mauve colored flowers;
3. Numerous single flowers;
4. Easily propagated by semi-hardwood cuttings in late spring through summer;

5. Moderate growth rate under normal fertilization and moisture conditions;
6. Broadly-rounded, compact in nature;
7. Grows well in containers;
8. Thrives in shade or sun; and
9. Hardy in Zone 6.

DESCRIPTION OF THE PHOTOGRAPHS

This new Azalea hybrid variety is illustrated by the accompanying photographs which show buds, flowers, immature foliage and mature foliage. The colors shown are as true as can be reasonably obtained by conventional photographic means. The photographs are of 6-year-old plants grown in filtered shade in September in 2009 in Dearing, Ga.

DETAILED BOTANICAL DESCRIPTION OF THE NEW PLANT

Figure 1:
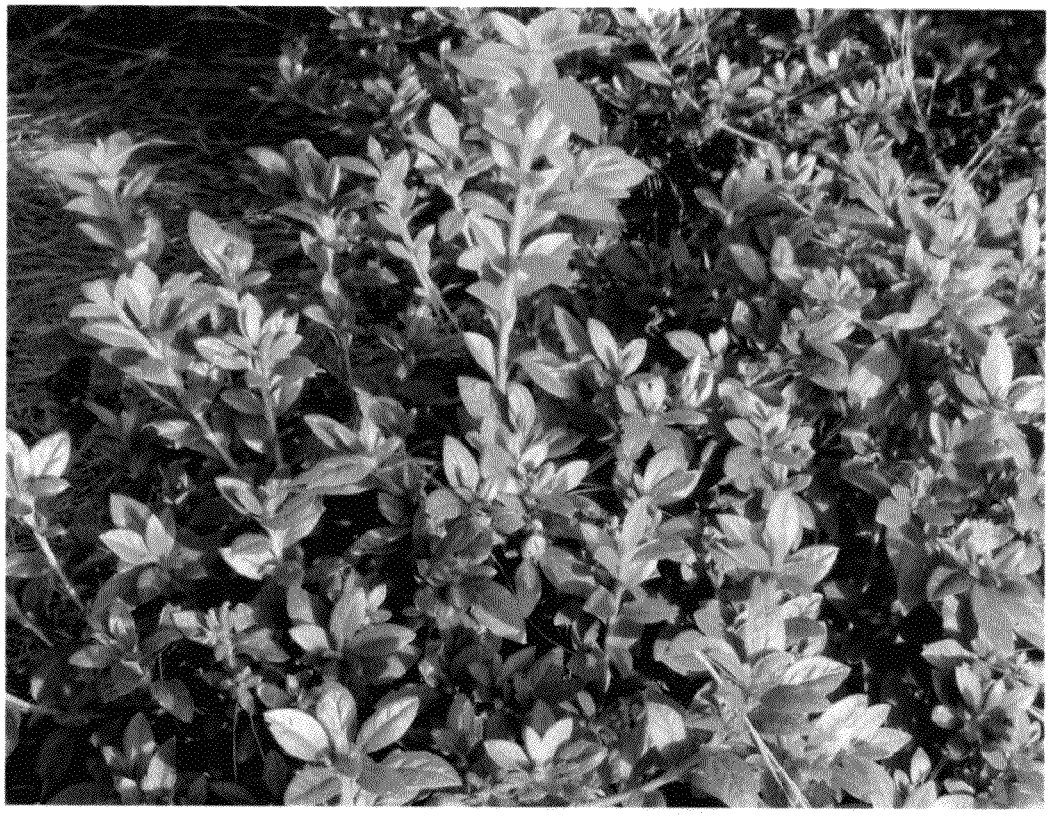
FIG. 1 is a close-up showing stems and mature foliage.
Figure 2:
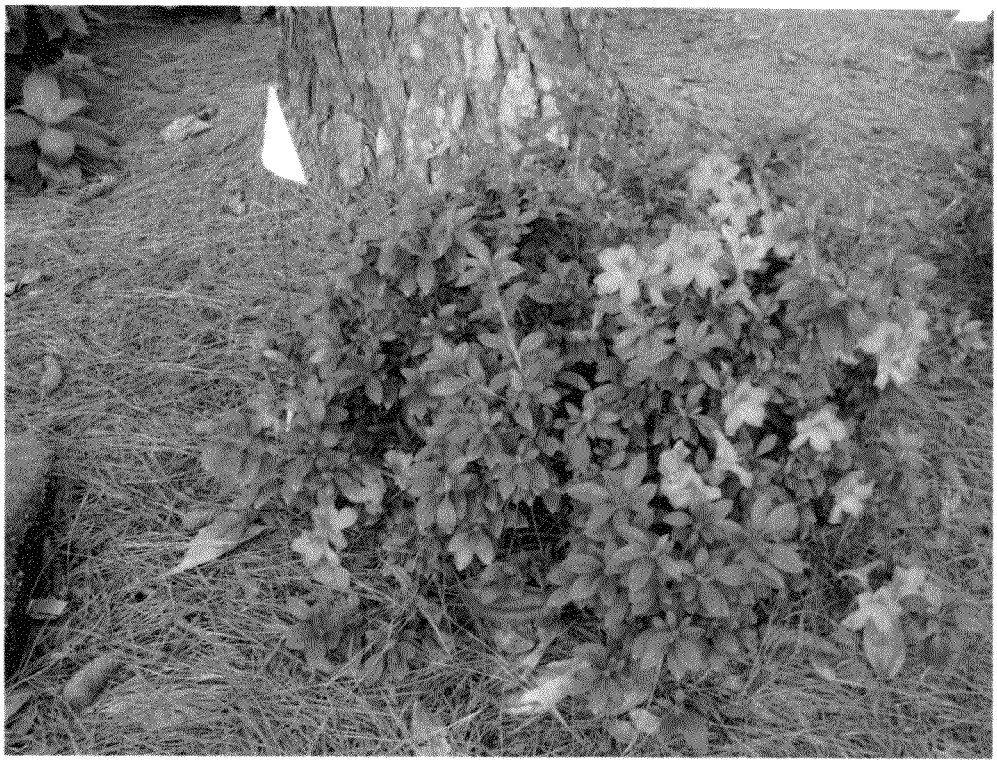
FIG. 2 shows mature foliage and growth habit of a five year old plant.
Figure 3:
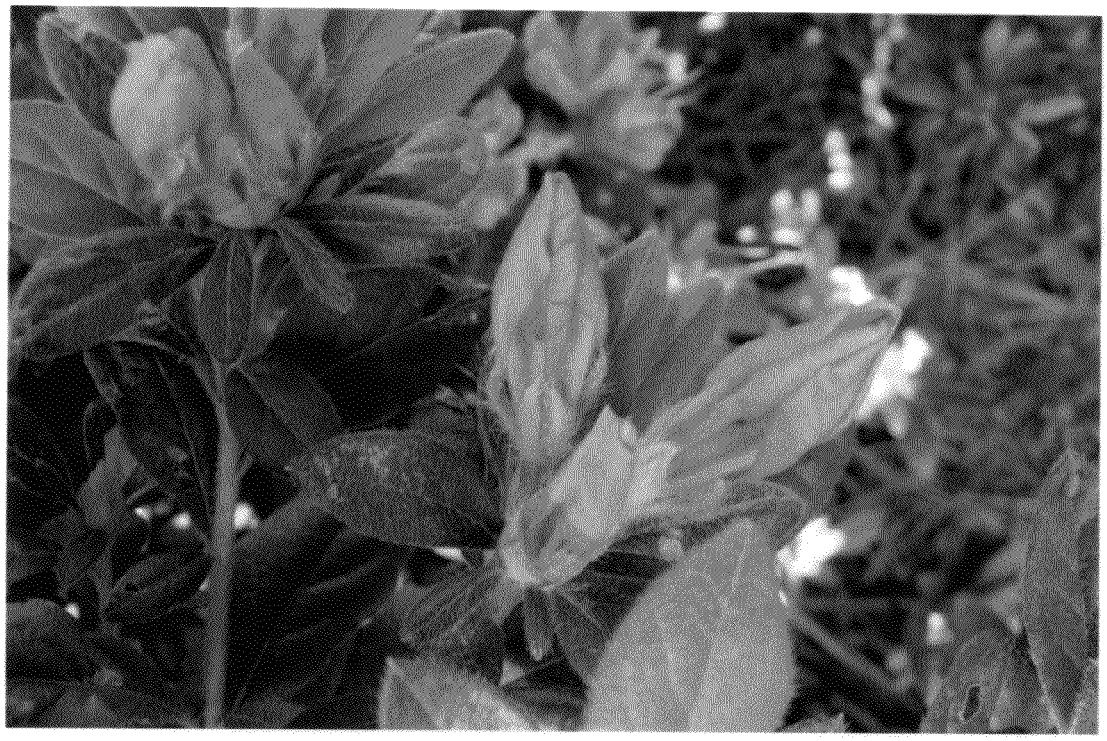
FIG. 3 is a close-up showing flower buds.
Figure 4:
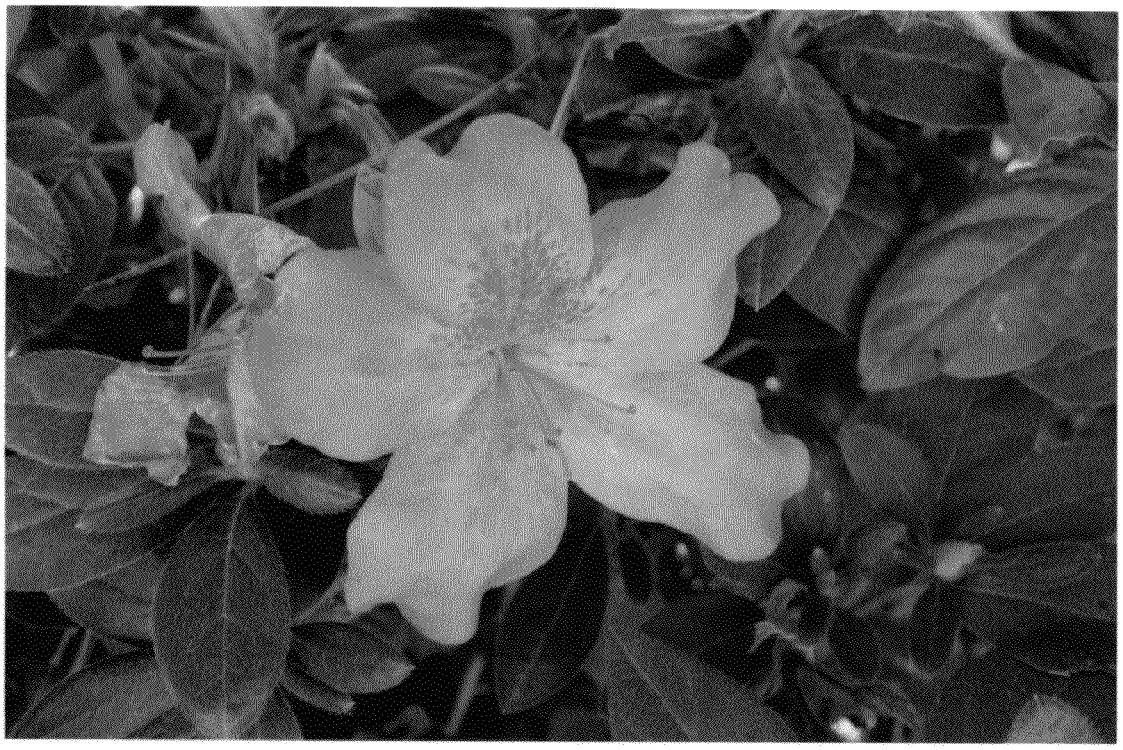
FIG. 4 is a close-up showing flower size, form, and color.

The following is a detailed description of the new variety of Azalea based on observations made of 4-year-old plants grown in three-gallon containers according to wholesale commercial production conditions, under full-sun, and in an evaluation bed under semi-shade conditions in Dearing, Ga. in spring, summer, and fall in 2009. The colors of the various plant parts are detailed with reference to The Royal Horticultural Society Colour Chart (2001).

Classification:

*Family*.—Ericaceae.
*Species*.—*Rhododendron* sp.
*Common name*.—Azalea.
*Commercial name*.—'MNIHAR014'.

Parentage:

*Female parent*.—The azalea plant 'Martha Hitchcock' (unpatented).

*Male parent*.—The azalea plant 'Conlec' (U.S. Plant Pat. No. 10,580).

Growth:

*Form*.—Broadly-rounded, compact in nature.

*Texture*.—Medium.

*Height*.—91.44 cm to 106.68 cm.

*Width*.—121.92 cm to 152.4 cm.

*Growth habit*.—Broadly-rounded and freely-branching.

*Growth rate*.—Moderate growth rate under normal fertilization and moisture conditions. In a period of five years from a rooted cutting the plant reaches a height of 60.96 cm and a spread of 106.68 cm. The growth rate is normally averages about 6.2 cm per year; the plant reaches a height of 91.44 cm to 106.68 cm at maturity while maintaining a dense habit due to the abundant branch development.

*Spring growth*.—The date of initial spring growth is March 25, followed by continuous growth through fall.

*Life cycle*.—Perennial and evergreen.

Leaves:

*Arrangement*.—Alternate, simple, pubescent, and evergreen.

*Shape*.—Elliptic to broadly elliptic.

*Apex*.—Acute.

*Base*.—Acuminate.

*Margin*.—Entire.

*Length*.—5.1 cm.

*Width*.—1.9 cm.

*Venation pattern*.—Pinnate; the mid-veins and laterals are impressed on the upper surface and the prominent on the lower surface.

*Venation color* (*both upper and lower surfaces*).—RHS 146C (yellow-green).

*Immature leaf*.—Upper surface: Color: Matte, RHS 144A (yellow-green). Pubescence: Strigose, moderate amount. Pubescence color: RHS 159B (orange-white). Lower surface: Color: Matte, RHS 146C (yellow-green). Pubescence: Strigose, moderate amount. Pubescence color: RHS 155C (white).

*Mature leaf*.—Upper surface: Color: Semi-glossy, RHS 147A (yellow-green). Pubescence: Hispid to strigose. Pubescence color: RHS 155C (white). Lower surface: Color: Matte, RHS 146B (yellow-green). Pubescence: Hispid to strigose. Pubescence color: RHS 164C (greyed-orange).

*Petiole*.—Length: 1.0 to 1.3 cm. Diameter: 0.15 cm. Pubescence: Pilose to strigose. Pubescence length: 0.1 cm. Pubescence color: Immature: RHS N159D (orange-white). Mature: RHS 165A (greyed-orange). Color: Immature: RHS N144A (yellow-green). Mature: RHS 146C (yellow-green).

Stems:

*Form*.—Densely branched at buds.

*Young stems* (*1-year-old and younger*).—Color: RHS 144B (yellow-green) and RHS N199C (grey-brown) with areas of RHS 151A (yellow-green), RHS 152D (yellow-green) and RHS N199D (grey-brown). Pubescence: Strigose. Pubescence color: RHS N155A (white) and RHS 164B (greyed-orange).

*Second-year stems*.—Stem and pubescence color: RHS N199A (grey-brown) and RHS N199B (grey-brown) with no pubescence present. Length: 5.8 cm on average. Diameter: 0.3 cm. Pith: Solid and uniform. Internode length: Average 1.3 cm.

Flower buds:

*Arrangement and form*.—Tight; borne in groups of three with some in groups of four and five sheathed by a pair of modified leaf bracts. Length: 1.4 cm. Width: 1.0 cm. Color: RHS 144A (green).

*Shape*.—Ovate.

*Apex*.—Acuminate.

*Base*.—Rounded.

*Length* (*at tight bud*).—1.3 cm.

*Diameter* (*at tight bud*).—0.6 cm.

*Bud scales*.—Length: 1.2 cm. Width: 0.7 cm.

*Color* (*of scales*).—Immature scales: RHS 144D (yellow-green). Mature: RHS 144C (yellow-green).

*Texture*.—Pubescent; scabrous and strigose pubescence. Pubescence color: RHS 164B (greyed-orange).

*Pedicel*.—Length: 1.2 cm. Diameter: 0.2 cm. Texture: Pilose pubescence. Pubescence color: RHS 159A (orange-white) and RHS 155A (white). Color: RHS 144A (yellow-green).

*Calyx*.—Form and arrangement: Composed of 5 sepals in a cup-shape. Length: 0.9 cm. Width: 1.3 cm. Color: RHS 144A (yellow-green). Pubescence: Pilose. Pubescence color: RHS N155A (white) in color. Sepals: Shape: Broadly elliptical to lanceolate. Apex: Acute. Base: Fused; joined at base to form a cup. Margin: Entire. Color: Upper surfaces: RHS 144A (yellow-green). Lower surfaces: RHS 145B (yellow-green). Length: 1.3 cm. Width: 0.3 cm.

Flowers:

*Type*.—Perfect, Single flowers.

*Shape*.—Open funnel-shaped.

*Flowering habit and period*.—Borne on the current season's growth; 3 weeks beginning in late March in Dearing, Ga.; flowering resumes in early August and continues until frost which can be as late as November or December.

*Lastingness of flowers on the plant*.—4 to 7 days in the sun; 6 to 9 days in the shade; flowers are self-cleaning.

*Fragrance*.—Absent.

*Diameter*.—5.3 cm.

*Depth*.—3.8 cm.

*Petals*.—Quantity per flower and arrangement: 5 imbricate petals that are fused at the base and remain fused up to 2.6 cm from the base. Shape: Obovate. Apex: Rounded. Base: Fused. Margin: Entire to undulate. Texture (both upper and lower surfaces): Glabrous. Length (of petals without spots): 3.5 cm. Width (of petals without spots): 2.1 cm. Length (of petals with spots): 3.2 cm. Width (of petals with spots): 2.1 cm. Color: Upper surfaces: RHS 70B (red-purple) and RHE 70C (red-purple) with spots of RHS 67A (red-purple). Lower surfaces: RHS 70B (red-purple) to 70C (red-purple); the lower spots are not visible.

Reproductive parts:

*Pistil*.—Quantity and form: Single, non-petaloid. Length: 3.9 cm. Diameter: 0.075 cm. Stigma: Color: RHS 152C (yellow-green). Diameter: 0.1 cm. Style color: RHS N170D (greyed-orange). Ovary: Pubescent, pilose, and with 5 locules. Color: RHS N155A (white).

*Stamens*.—Number: 5 per flower. Length: 2.9 cm. Color: RHS 65C (red-purple). Filament: RHS 65C (red-purple); 2.8 cm in length. Anther: Length: 0.3 cm. Width: 0.1 cm. Color: RHS N77A (purple). Pollen: Abundant; RHS 155D (white).

Fruit:

*Maturity*.—The capsule matures in about 6 months in Dearing, Ga. and the fruit set is moderate and contains about 100-300 non-winged seeds.

*Length*.—1.5 cm.

*Width*.—0.7 cm.

*Color*.—RHS 146B (yellow-green).

CULTURE

'MNIHAR014' grows well in a wide range of conditions and tolerates sun to shade. 'MNIHAR014' prefers moist, well-drained soil that is rich in organic matter and responds well to mulching and medium applications of fertilizer. 'MNIHAR014' does best in soil with a pH of 5.0 to 5.5 and is propagated with semi-hardwood cuttings in late spring through the summer. Azaleas root in five to six weeks with a high percentage of rooting (80% plus). Tissue culture is also an effective means of propagation for azaleas.

DISEASES AND INSECTS

Lace bugs, root weevils, and spider mites can be a problem. Fungal and bacterial pathogens have not been observed, but no resistance testing has been performed and no claim to abnormal resistance to pathogens can be made.

COMPARISON WITH PARENTAL AND COMMERCIAL VARIEITES

When 'MNIHAR014' is compared to the commercial variety 'Roblen' (U.S. Plant Pat. No. 16,248), 'MNIHAR014' has faster and broader growth habit with a height of 60.96 cm and a spread of 106.68 cm in five years; whereas 'Roblen' (U.S. Plant Pat. No. 16,248) has a height of 91.44 cm and a spread of 60.96 cm in six years. Additionally, 'MNIHAR014' produces mauve flowers, while 'Roblen' has bright red flowers.

In Table 1, the 'MNIHAR014' is compared to parental varieties 'Martha Hitchcock' (unpatented) and 'Conlec' (U.S. Plant Pat. No. 10,580) and lists the differences between the varieties.

TABLE 1

| Characteristic | 'MNIHAR014' | 'Martha Hitchcock' | 'Conlec' |
|---|---|---|---|
| Plant Height (Mature) | 91.44 cm to 106.68 cm | 91.44 cm | 183 cm to 244 cm |
| Flower Diameter | 5.3 cm | 7.62 cm | 8.9 cm to 10.1 cm |
| Flower Form | Single | Single | Single |
| Flower Color | Mauve | White with purple margin | Purple |
| Bloom Period | Late-March to April and Early August until frost | April | Mid April to May and sporadic in the summer until frost |
| Hardy Zone | 6 | 6 | 7 |
| Stamen Number | 5 | 5 | 8 to 10 |
| Stamen Type | Non-petaloid | Non-petaloid | Non-petaloid |

I claim:

1. A new variety of Azalea plant named 'MNIHAR014' as herein shown and described.

* * * * *